United States Patent
Yamanaka et al.

(10) Patent No.: US 9,389,218 B2
(45) Date of Patent: Jul. 12, 2016

(54) MEASURING DEVICE, DIALYSIS END CONDITION DETERMINING DEVICE, AND DIALYSIS PROGRESS PRESENTING DEVICE

(71) Applicants: Sharp Kabushiki Kaisha, Osaka-shi, Osaka (JP); Ryoji Nagai, Kikuchigun (JP)

(72) Inventors: Mikihiro Yamanaka, Osaka (JP); Keita Hara, Osaka (JP); Ryoji Nagai, Kikuchigun (JP)

(73) Assignees: Sharp Kabushiki Kaisha, Osaka (JP); Ryoji Nagai, Kumamoto (JP)

( * ) Notice: Subject to any disclaimer, the term of this patent is extended or adjusted under 35 U.S.C. 154(b) by 0 days.

(21) Appl. No.: 14/381,635

(22) PCT Filed: Mar. 8, 2013

(86) PCT No.: PCT/JP2013/056456
§ 371 (c)(1),
(2) Date: Aug. 28, 2014

(87) PCT Pub. No.: WO2013/146188
PCT Pub. Date: Oct. 3, 2013

(65) Prior Publication Data
US 2015/0044099 A1     Feb. 12, 2015

(30) Foreign Application Priority Data
Mar. 30, 2012   (JP) .................. 2012-081904

(51) Int. Cl.
G01N 33/49     (2006.01)
G01N 21/64     (2006.01)
(Continued)

(52) U.S. Cl.
CPC .......... *G01N 33/4915* (2013.01); *A61B 5/1455* (2013.01); *A61B 5/14546* (2013.01);
(Continued)

(58) Field of Classification Search
CPC .............. G01N 33/4915; G01N 33/53; G01N 21/6486; G01N 33/491; A61K 35/12; A61B 5/1455; A61M 1/14; A61M 1/367
USPC ......................................... 422/82.08; 424/520
See application file for complete search history.

(56) References Cited

U.S. PATENT DOCUMENTS 3,659,629 A * 5/1972 Deaton ............. A61M 5/16822
                                                        137/551
4,013,072 A * 3/1977 Jess ..................... A61M 5/165
                                                        137/177
(Continued)

FOREIGN PATENT DOCUMENTS

JP      06-312134 A     11/1994
JP      2009-269887 A   11/2009
(Continued)

OTHER PUBLICATIONS

Official Communication issued in International Patent Application No. PCT/JP2013/056456, mailed on Apr. 16, 2013.

*Primary Examiner* — Jill Warden
*Assistant Examiner* — Jacqueline Brazin
(74) *Attorney, Agent, or Firm* — Keating & Bennett, LLP

(57) ABSTRACT

A measuring device (10) includes an analysis unit (101) that holds a fluid pool (B) of blood or serum therein, an irradiation unit (105) that irradiates fluorescent substances contained in the fluid pool (B) with excitation light, and a light receiving unit (106) that receives fluorescence generated from the fluorescent substances. An amount of the fluorescent substances contained in the blood or the serum after artificial dialysis is estimated from the intensity of the fluorescence.

9 Claims, 7 Drawing Sheets

(51) Int. Cl.
*A61M 1/14* (2006.01)
*A61M 1/36* (2006.01)
*A61B 5/145* (2006.01)
*A61B 5/1455* (2006.01)

(52) U.S. Cl.
CPC ............... *A61M 1/14* (2013.01); *A61M 1/367* (2013.01); *G01N 21/6486* (2013.01); *G01N 33/491* (2013.01); *A61M 2205/3313* (2013.01); *A61M 2230/20* (2013.01); *G01N 2201/062* (2013.01); *G01N 2201/06113* (2013.01); *G01N 2201/08* (2013.01)

(56) References Cited

U.S. PATENT DOCUMENTS

| | | | |
|---|---|---|---|
| 4,395,260 A * | 7/1983 | Todd et al. | 604/122 |
| 6,007,690 A * | 12/1999 | Nelson et al. | 204/601 |
| 6,159,186 A * | 12/2000 | Wickham | A61M 5/1689 604/251 |
| 6,592,821 B1 * | 7/2003 | Wada et al. | 422/68.1 |
| 7,572,640 B2 * | 8/2009 | Goix et al. | 436/172 |
| 7,955,504 B1 * | 6/2011 | Jovanovic et al. | 210/321.71 |
| 2004/0057037 A1 * | 3/2004 | Ohishi | A61M 1/16 356/39 |
| 2007/0043325 A1 * | 2/2007 | Guala | A61M 5/1411 604/252 |
| 2010/0168925 A1 | 7/2010 | Hilgers et al. | |
| 2011/0020459 A1 * | 1/2011 | Achrol et al. | 424/520 |
| 2012/0095433 A1 * | 4/2012 | Hungerford | A61M 5/1689 604/500 |
| 2012/0190945 A1 | 7/2012 | Yamanaka et al. | |
| 2014/0267709 A1 * | 9/2014 | Hammond | G01N 21/85 348/143 |

FOREIGN PATENT DOCUMENTS

| | | |
|---|---|---|
| JP | 2009-539440 A | 11/2009 |
| JP | 2011 196848 * | 10/2011 |
| JP | 2011-196848 A | 10/2011 |
| WO | 2011/040599 A1 | 4/2011 |

\* cited by examiner

F I G. 5
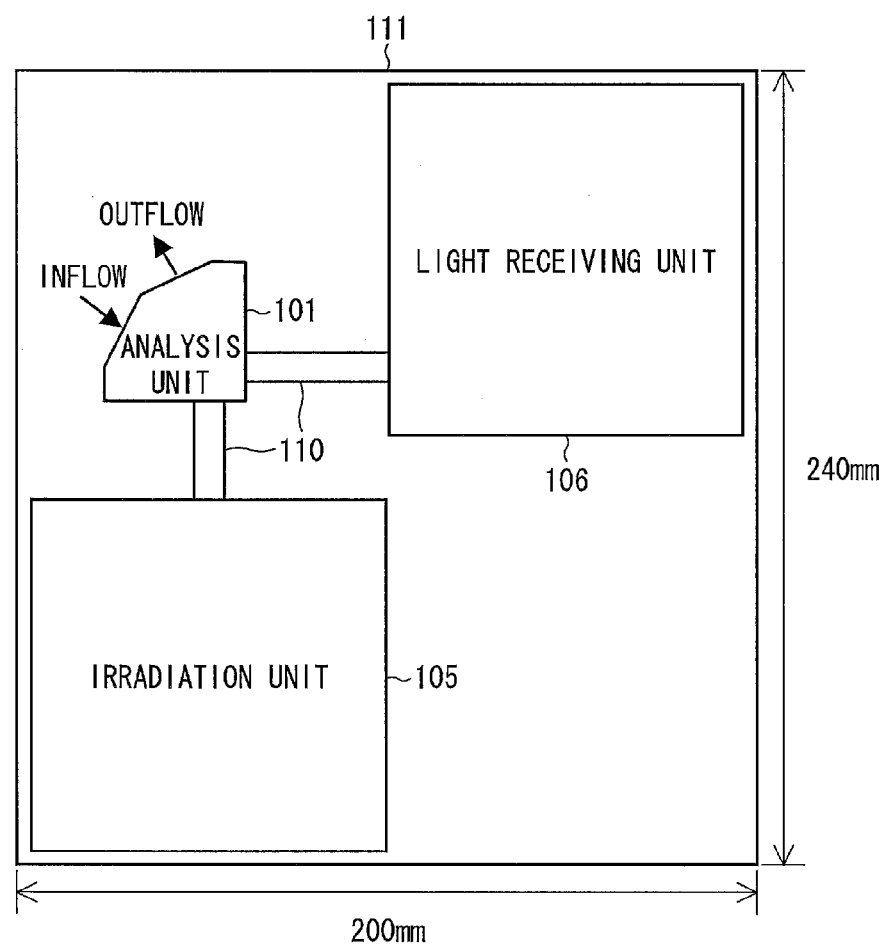

F I G. 6
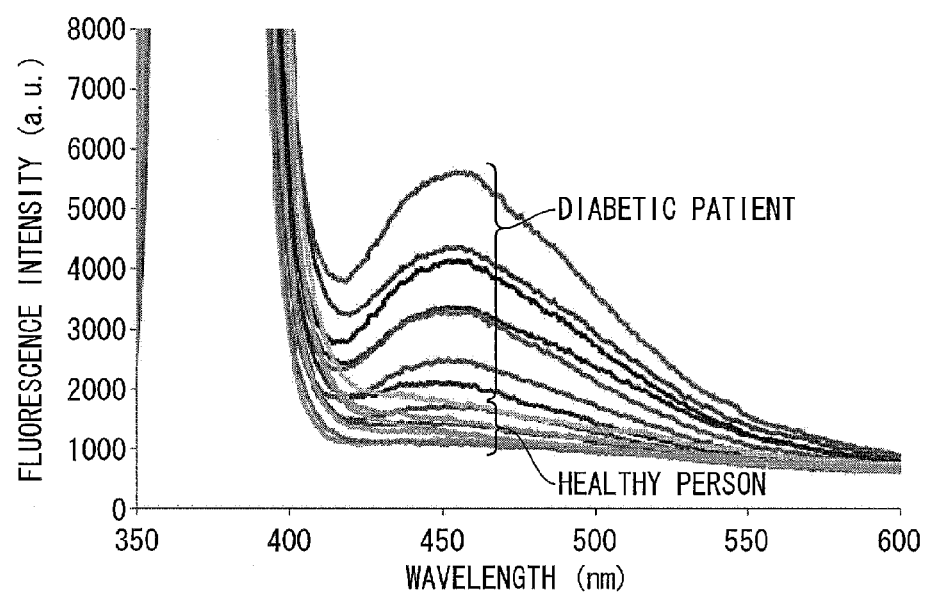

MEASURING DEVICE, DIALYSIS END CONDITION DETERMINING DEVICE, AND DIALYSIS PROGRESS PRESENTING DEVICE

TECHNICAL FIELD

The present invention relates to a measuring device for monitoring AGEs during artificial dialysis, a dialysis end condition determining device for determining an end condition of artificial dialysis, and a dialysis progress presenting device for presenting the progress of artificial dialysis.

BACKGROUND ART

In recent years, with westernization of diets, patients of lifestyle-related diseases are increasing and resulting in serious medical and social problems. At present, in Japan, the number of diabetic patients is 8,000,000. It is also said that the number of diabetic patients plus pre-diabetic patients reaches 20,000,000. The three main complications of diabetes are "retinopathy, nephropathy, and neuropathy". Diabetes is also a cause for arteriosclerosis. Furthermore, diabetes may cause heart diseases and brain diseases.

A person develops diabetes in such a manner that improper diets and life styles, secretion from fat cells due to fatness, or oxidative stress decreases the function of pancreas, causing shortage of insulin that controls a blood glucose level or reducing the effect of insulin. Diabetes has symptoms such as frequent urination, an increased amount of urination, and increased thirst. However, such symptoms may not enable patients to realize that they have developed diabetes, and most patients know their illness when they undergo examination in hospitals, etc. This explains why there are so many "silent" diabetic patients.

At the stage where abnormal symptoms resulting from the complications of diabetes are found in hospitals, etc., conditions of the disease have advanced too far, making it difficult to completely cure the disease. In particular, many of the complications of diabetes are difficult to cure, and therefore prevention of diabetes is considered as important as many other life-style related diseases. For the prevention, early identification and early determination of therapeutic effect are essential, and there are many inspections for diabetes for that purpose.

In a situation where blood contains abnormal amounts of carbohydrates and lipids therein, protein reacts with the carbohydrates and the lipids so that AGEs (Advanced Glycation Endproducts) are produced. AGEs are end products produced via non-enzymatic glycosylation reaction of protein (Maillard reaction). AGEs emit fluorescence and form crosslinks by bonding to nearby proteins.

AGEs are considered to be directly deposited on and infused into blood vessel walls or to interact with macrophage which is a part of an immune system, to thereby release cytokine that is one type of protein and to cause inflammation, resulting in arteriosclerosis.

Diabetic patients are concurrently associated with disorder of the kidney in many cases if they do not receive any medial treatment after the onset of diabetic. Therefore, the diabetic patients are required to receive treatment with artificial dialysis. In such artificial dialysis, it is preferable to remove not only target substances that have been removed so far by the artificial dialysis, but also AGEs with the view of preventing the above-mentioned diseases attributable to AGEs. PTL 1 discusses the problem that AGEs are accumulated in peritoneal tissues with peritoneal dialysis, which is one method of the artificial dialysis. PTL 2 discloses an absorbent capable of adsorbing and removing glycation-denatured protein that is contained in a body fluid.

CITATION LIST

Patent Literature

PTL 1: Japanese Unexamined Patent Application Publication No. 2009-269887 (Laid-open on Nov. 19, 2009)
PTL 2: Japanese Unexamined Patent Application Publication No. 6-312134 (Laid-open on Nov. 8, 1994)

SUMMARY OF INVENTION

Technical Problem

The inventors have confirmed the new finding that AGEs are contained in serum as well after the artificial dialysis. This implies that more appropriate management of the artificial dialysis can be realized if there is a device monitoring AGEs contained in serum after the artificial dialysis or in blood circulated during the artificial dialysis. However, PTL 1 and PTL 2 do not disclose such a device.

In view of the problems described above, an object of the present invention is to provide a measuring device for monitoring AGEs in blood or serum, a dialysis end condition determining device using the measuring device, and a dialysis progress presenting device using the measuring device.

Solution to Problem

To solve the problems described above, the present invention according to one aspect provides a measuring device comprising an analysis unit that holds blood or serum therein, an irradiation unit that irradiates fluorescent substances in the blood or the serum with excitation light, and a light receiving unit that receives fluorescence generated upon irradiation with the excitation light.

Advantageous Effects of Invention

According to one aspect of the present invention, as described above, the measuring device includes an analysis unit that holds blood or serum therein, an irradiation unit that irradiates fluorescent substances in the blood or the serum with excitation light, and a light receiving unit that receives fluorescence generated upon irradiation with the excitation light.

Therefore, the artificial dialysis can be more appropriately managed by incorporating the measuring device according to the present invention, as a device for monitoring an amount of AGEs during the dialysis, into an artificial dialysis system. For example, a dialysis time and a degree of the dialysis, which have been so far determined at the discretion of a doctor, can be controlled in accordance with objective data. In addition, more appropriate management of the artificial dialysis can be realized by determining the end of the artificial dialysis such that AGEs will not remain in the blood.

BRIEF DESCRIPTION OF DRAWINGS

FIG. 5 illustrates a layout and an approximate size of the measuring device of FIG. 1 in an actually practiced form.

FIG. 6 is a graph depicting measurement results of fluorescence attributable to AGEs in serums of a diabetic patient and a healthy person.

DESCRIPTION OF EMBODIMENTS

One embodiment of the present invention will be described below with reference to FIGS. 1 to 7.

<Configuration of Dialysis System 1>

Figure 2:
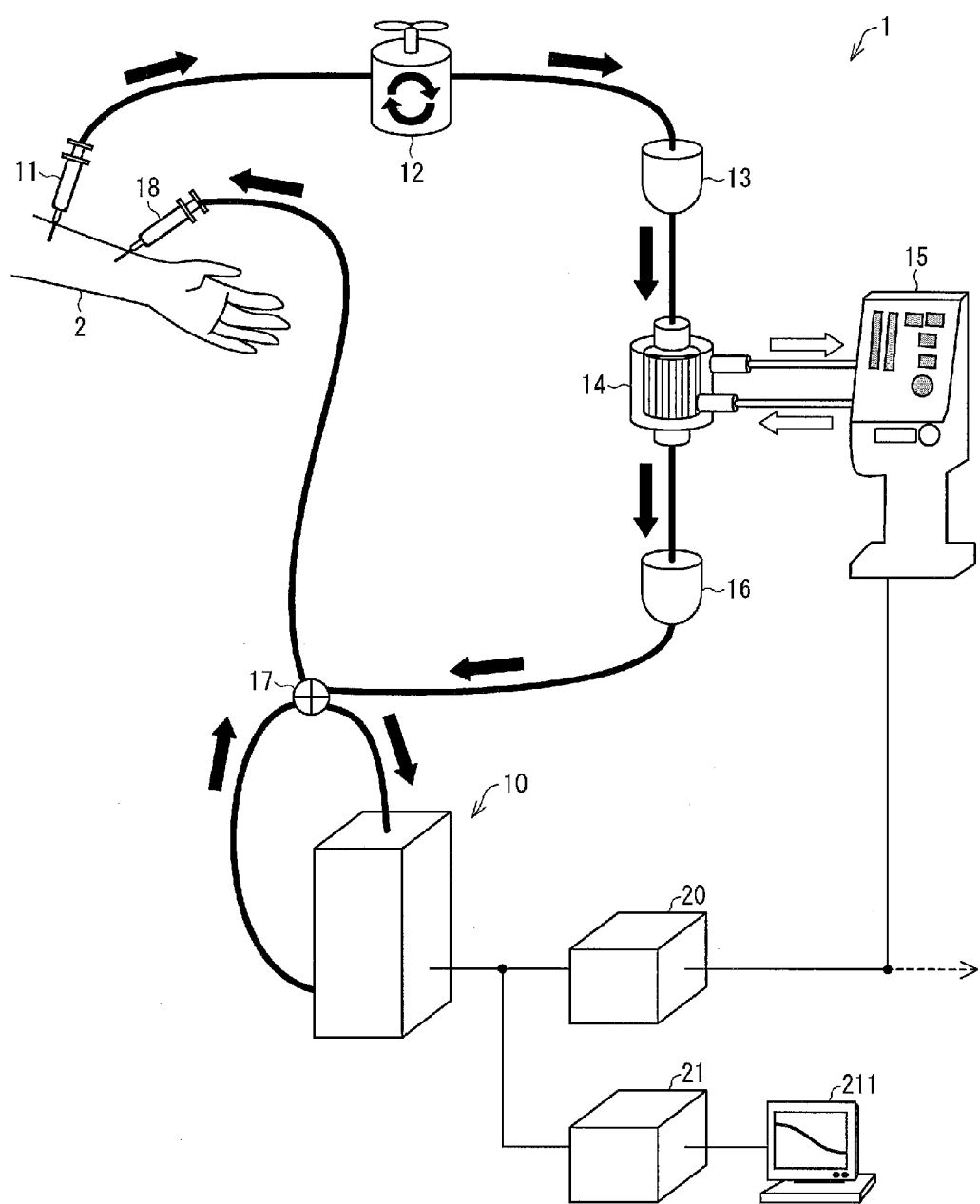
FIG. 2 illustrates a basic configuration of a dialysis system according to one embodiment of the present invention.

FIG. 2 illustrates a basic configuration of a dialysis system 1 according to one embodiment of the present invention. As illustrated in FIG. 2, the dialysis system 1 includes, as system components, an artery shunt 11 inserted to an artery of an arm 2 that is an object of artificial dialysis, a blood pump 12, an artery-side drip chamber 13, a dialyzer 14, a vein-side drip chamber 16, a branch valve 17, and a vein shunt 18 inserted to a vein of the arm 2 that is the object of the artificial dialysis. In the dialysis system 1, those system components are interconnected by tubes, etc., and the dialysis is performed with blood circulated through the system components in the above-mentioned order. The dialysis system 1 further includes a measuring device 10, a dialysis device 15, a dialysis end condition determining device 20, and a dialysis progress presenting device 21. In addition, a pump, etc. for injecting an anticoagulant into the blood may be disposed upstream of the blood pump 12. The measuring device 10, the dialysis device 15, the dialysis end condition determining device 20, and the dialysis progress presenting device 21 are interconnected by tubes and communication lines such that, among the system components, the blood can be circulated and data can be transmitted and received.

The artery shunt 11 is an appliance to extract the blood from the artery of the arm 2 that is the object of the artificial dialysis. A needle, which is inserted to the artery, and a tube are connected to the artery shunt 11. The vein shunt 18 is an appliance to return the blood to the vein of the arm 2. A needle, which is inserted to the vein, and a tube are connected to the vein shunt 18. By inserting the needle of the artery shunt 11 to the artery and inserting the needle of the vein shunt 18 to the vein, the object of the artificial dialysis is smoothly connected to the dialysis system 1 such that the blood can be circulated in the dialysis system 1.

The blood pump 12 serves to apply pressure necessary for executing the artificial dialysis to the blood. The blood is pressurized by the blood pump 12 so as to flow at a rate of 150 to 300 ml/min, for example.

In general, a drip chamber has a flow passage with a larger diameter than that of a flow passage through which the circulated blood flows, and it temporarily holds the blood flowing into there. The drip chamber temporarily holding the blood captures foreign matters, such as bubbles and thrombi, before the blood flows out from the inside of the drip chamber. Therefore, the drip chamber is also called an air trap.

More specifically, the artery-side drip chamber 13 serves to prevent foreign matters, such as bubbles and thrombi, from being mixed into the dialyzer 14 from a blood extracting line.

In the case of no necessity of measuring the artery pressure, the inside of the artery-side drip chamber 13 is preferably fully filled with the blood such that the blood does not contact air, without adjusting a surface level of the blood temporarily held in the analysis unit 13.

The vein-side drip chamber 16 serves to prevent foreign matters, such as bubbles and thrombi, from being mixed into the object of the artificial dialysis from a blood returning line after the blood has flowed out from the dialyzer 14. In the vein-side drip chamber 16, a surface position of the blood inside the vein-side drip chamber 16 is adjusted such that the surface position of the blood temporarily held in the chamber is located at about 80% of a total height of the chamber. With that adjustment, the vein pressure can be measured. Moreover, a drug solution line may be disposed upstream of the vein-side drip chamber 16, and a drug may be supplied, through the drug solution line, to the blood held in the vein-side drip chamber 16.

The dialyzer 14 dialyzes the blood by utilizing a cellophane membrane (semipermeable membrane) or a hollow fiber membrane. The cellophane membrane has a property of selectively allowing a particular component of a solution to pass therethrough, but not allowing other components to pass therethrough. By arranging the cellophane membrane in a state partitioning the blood and a dialysis liquid from each other, a harmful substance, e.g., uremic toxin, can be moved from the blood to the dialysis liquid and can be removed from the blood by utilizing the above-mentioned property of the cellophane membrane. The hollow fiber membrane is constituted by hollow fibers made of synthetic resin. Each of the hollow fibers has a straw-like shape, and numerous ultra-fine holes are formed in a wall surface of the hollow fiber. By causing the blood to flow through the inside of the hollow fiber and filling the outside of the hollow fiber with the dialysis liquid, a harmful substance, e.g., uremic toxin, can be moved from the blood to the dialysis liquid and can be removed from the blood as with the cellophane membrane.

The dialysis device 15 supplies the dialysis liquid to the dialyzer 14. The dialysis liquid supplied from the dialysis device 15 is circulated between the dialyzer 14 and the dialysis device 15 and is successively replaced with a fresh dialysis liquid in the dialysis device 15. The dialysis liquid is produced in the dialysis device 15 where tap water and a dialysis liquid concentrate are mixed with each other at a certain ratio. Furthermore, the dialysis device 15 is required to perform the dialysis in safety. In more detail, the dialysis device 15 monitors the temperature and the flow rate of the dialysis liquid, the pressure in a blood circuit, leakage of the blood, etc. If there is an abnormality in concentration of the dialysis liquid, etc., the dialysis device 15 issues an alarm using a buzzer, for example, and stops the artificial dialysis. The dialysis liquid is controlled by the dialysis device 15 so as to flow at a rate of 500 to 800 ml/min, for example.

<Configuration of Measuring Device 10>

Figure 1:
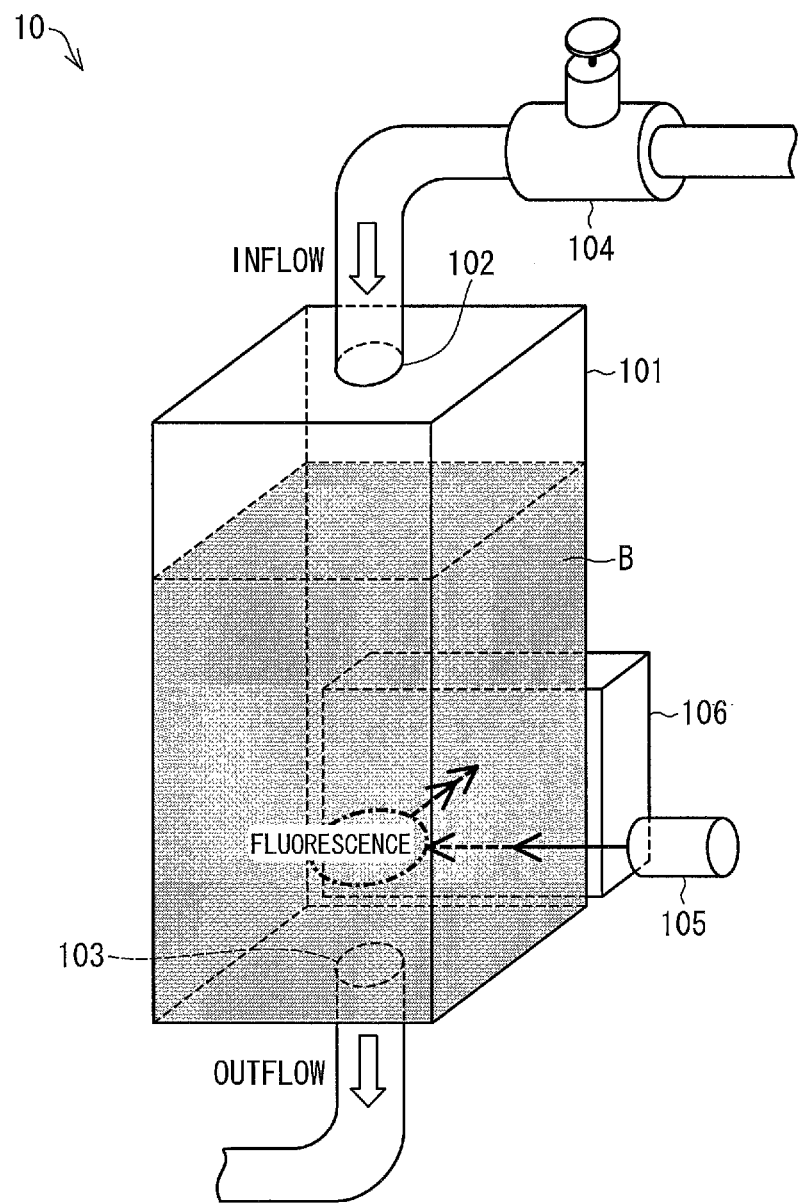
FIG. 1 is a conceptual view illustrating a configuration of a measuring device according to one embodiment of the present invention.

FIG. 1 is a conceptual view illustrating a configuration of the measuring device 10 according to one embodiment of the present invention. As illustrated in FIG. 1, the measuring device 10 includes an analysis unit 101 for holding blood therein, a regulator 104, an irradiation unit 105, and a light receiving unit 106. In the dialysis system 1, the measuring device 10 is connected to a portion of the dialysis system 1, which is branched by the branch valve 17 (see FIG. 2).

As illustrated in FIG. 1, an inflow port 102 and an outflow port 103 are formed in the analysis unit 101. During the artificial dialysis, the blood flows into the analysis unit 101 through the inflow port 102 and flows out from the analysis unit 101 through the outflow port 103. On that occasion, when inflow of the blood and outflow of the blood are in an equilibrium state, a fluid pool B is formed inside the analysis unit 101. In the measuring device 10, by irradiating the fluid pool B with excitation light emitted from the irradiation unit 105, fluorescent substances in the blood are excited to generate fluorescence. By receiving the generated fluorescence by the light receiving unit 106, the measuring device 10 measures the intensity of the fluorescence generated from the fluorescent substances in the blood.

In order to accurately measure the intensity of the fluorescence generated upon excitation of the fluorescent substances in the blood, the excitation light is preferably applied to the blood substantially in a standstill state. Stated in another way, the flow rate of the blood inside the fluid pool B is preferably substantially 0.

An amount of the fluid pool B is required to be at least a value at which the intensity of the fluorescence generated upon the irradiation with the excitation light is at an actually measurable level. It is therefore preferable that the analysis unit 101 has a capacity capable of forming the fluid pool B in the required amount. In practice, the generated fluorescence can be measured if there is blood of about 50 μl. However, a blood amount is not limited to such an exemplary value. When outer dimensions of the analysis unit 101 are about 5.5 mm×5.5 mm×30 mm, for example, the capacity of the analysis unit 101, which is actually usable to hold the blood, is about 200 μl (in this case, an optical path length of about 3 mm can be ensured for each of the excitation light and the fluorescence). In the analysis unit 101 described above, the fluorescence can be measured, for example, when the fluid pool B is formed in amount corresponding to half the capacity, i.e., when the blood amount is about 100 μl.

While FIG. 1 illustrates the analysis unit 101 in the form of a quadrangular prism, the shape of the analysis unit 101 is not limited to the illustrated one. As another example, the analysis unit 101 may have a triangular prism shape or a cylindrical shape. In other words, the analysis unit 101 may have any desired shape insofar as the blood can be irradiated with the excitation light and the fluorescence generated from the blood can be measured. In general fluorescence measurement, as illustrated in FIG. 1, the direction in which the blood is irradiated with the excitation light from the irradiation unit 105 is perpendicular to the direction in which the fluorescence is received by the light receiving unit 106. However, the direction irradiated with the excitation light and the direction of receiving the fluorescence are not necessarily required to be perpendicular to each other, and both the directions may be changed case by case such that the intensity of the fluorescence can be measured at a proper level.

Figure 3:
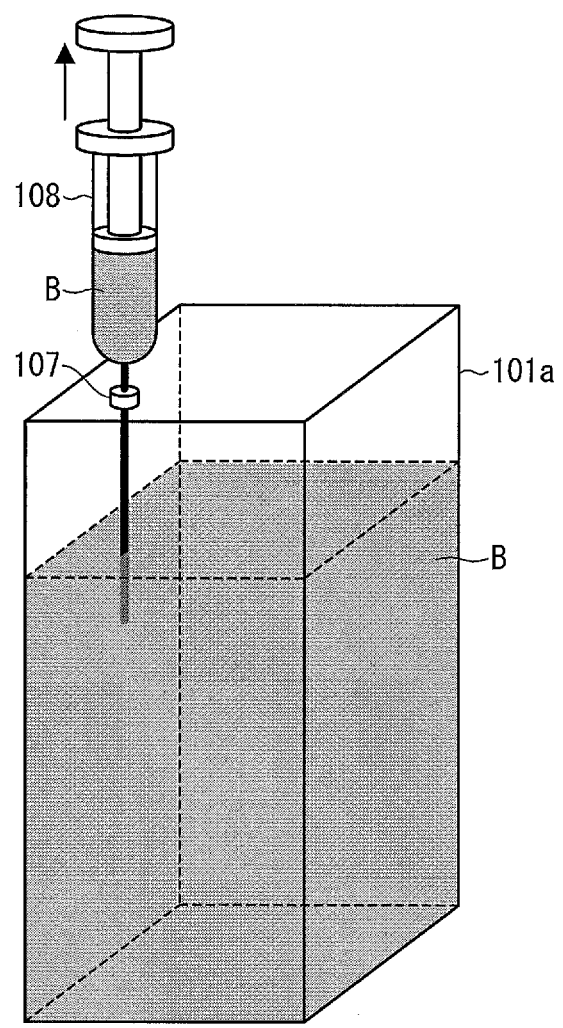
FIG. 3 illustrates a modification of an analysis unit equipped in the measuring device of FIG. 1.

FIG. 3 illustrates an analysis unit 101a as a modification of the analysis unit 101 equipped in the measuring device 10. As illustrated in FIG. 3, the analysis unit 101a includes a syringe sampling portion 107 (hole). The syringe sampling portion 107 is a hole formed in an upper surface of the analysis unit 101a such that a part of a syringe 108 is inserted into the analysis unit 101a through the hole. By inserting the syringe 108 through the syringe sampling portion 107, the blood can be sampled from the fluid pool B.

A position where the syringe sampling portion 107 is formed is not limited to the position illustrated in FIG. 3. For example, the syringe sampling portion 107 may be formed at a position other than the upper surface of the analysis unit 101a in combination with a structure including a check valve, etc. to prevent the blood from leaking from the analysis unit 101a.

When the blood is sampled as described above, serum, for example, can be obtained by subjecting the sampled blood to centrifugal separation. Furthermore, the sampled serum may be subjected to, e.g., liquid chromatography to analyze respective amounts and structures of fluorescent substances that are contained in the sampled blood or serum. The analysis result may be compared with the result of the above-described measurement of the fluorescence intensity.

The usage of the measuring device 10 is not limited to the case where the measuring device 10 is used inside the dialysis system 1. For example, after closing the outflow port 103 in the measuring device 10 and filling the blood in the analysis unit 101, the measuring device 10 may be removed from the dialysis system 1, and fluorescence generated from the blood may be measured in an offline state by irradiating the blood in the analysis unit 101 with the excitation light.

When fluorescence is measured in a small-sized flow passage, the size of the analysis unit 101 is also small, and the irradiation unit 105 and the light receiving unit 106 are positioned relatively close to each other. In such a case, the irradiation unit 105 and the light receiving unit 106 may be assembled in one probe. With that arrangement, the positional relationship between the irradiation unit 105 and the light receiving unit 106 is fixedly held, and the fluorescence can be stably measured.

The analysis unit 101 is preferably made of quartz. It is known that quartz is highly permeable to light over a wide range of wavelength including ultraviolet rays. With the analysis unit 101 being made of quartz, the excitation light passes through the analysis unit 101 with higher transmittance. Therefore, the fluorescent substances in the analysis unit 101 are more strongly excited, and stronger fluorescence is generated from the same amount of fluorescent substances. The stronger fluorescence thus generated passes through the analysis unit 101 with higher transmittance, and is received by the light receiving unit 106. Accordingly, the amount of the fluorescent substances in the blood or the serum can be satisfactorily estimated from the measurement result of the fluorescence intensity.

In the drip chamber, the flow rate of the blood is close to 0. Therefore, the fluorescence generated by exciting the fluorescent substances in the blood can be accurately estimated by employing the drip chamber as the analysis unit 101.

Figure 4:
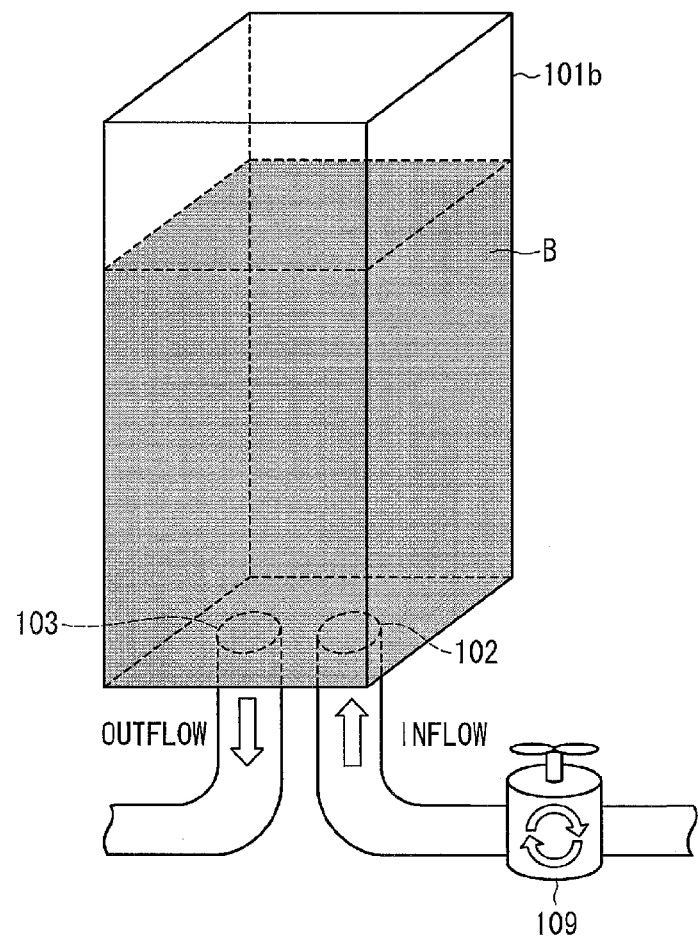
FIG. 4 illustrates another modification of the analysis unit equipped in the measuring device of FIG. 1.

The inflow port 102 is an entrance through which the blood flows into the analysis unit 101. While, in the configuration illustrated in FIG. 1, the inflow port 102 is formed in a central portion of the upper surface of the analysis unit 101, a position where the inflow port 102 is formed is not limited to the illustrated position. As another example, the inflow port 102 may be formed in any of an end portion of the upper surface, a side surface, or a lower surface of the analysis unit 101. When the inflow port 102 is formed in the lower surface of the analysis unit 101, the blood can be caused to efficiently flow into an analysis unit 101b by disposing a blood pump 109 as illustrated in FIG. 4.

The outflow port 103 is an exit through which the blood flows out from the analysis unit 101. While, in the example illustrated in FIG. 1, the outflow port 103 is formed in a central portion of the lower surface of the analysis unit 101, a position where the outflow port 103 is formed is not limited to the illustrated position. As another example, the outflow port 103 may be formed in any of an end portion of the lower surface, a side surface, or an upper surface of the analysis unit 101. Moreover, while, in the example illustrated in FIG. 1, the outflow port 103 is formed in a surface facing the inflow port 102, the positional relationship between both the ports is not limited to the illustrated one. As another example, the outflow port 103 and the inflow port 102 may be positioned in the lower surface of the analysis unit 101b, as illustrated in FIG.

4. Alternatively, the outflow port 103 and the inflow port 102 may be positioned in the upper surface or the same side surface of the analysis unit 101.

The regulator 104 regulates the flow rate of the blood flowing into the analysis unit 101. As illustrated in FIG. 1, the regulator 104 is in the form of a needle valve, and the flow rate of the blood can be regulated by screwing a needle. For example, when the blood is circulated in the dialysis system 1 at a flow rate of 150 to 300 ml/min (first flow rate), the blood may be decelerated by the regulator 104 such that the flow rate of the blood flowing into the analysis unit 101 is 10 ml/min or below (second flow rate).

The irradiation unit 105 applies the excitation light to the fluorescent substances (such as AGEs) in the blood that is held in the analysis unit 101. The irradiation unit 105 may be a filament lamp, an LED light source, or a laser light source. Alternatively, when excitation light emitted from the LED light source or the laser light source is guided from the outside of the measuring device 10 through a light guide means, e.g., an optical fiber, a distal end portion of the light guide means may be called the irradiation unit 105.

The light receiving unit 106 receives the fluorescence generated from the fluorescent substances in the blood, which are excited upon irradiation with the excitation light. The fluorescence generated from each fluorescent substance has a specific wavelength corresponding to the fluorescent substance. Thus, whether a particular fluorescent substance is contained in the blood can be confirmed by examining the wavelength at which a spectrum of the fluorescence intensity exhibits a peak. The light receiving unit 106 may be connected to a spectrometer to examine the wavelength exhibiting the peak intensity. The spectrometer may be, e.g., SEC2000-UV/IS (made by BAS Inc.).

<Device Configuration>

FIG. 5 illustrates a layout and an approximate size of the measuring device 10 in an actually practiced form in a state looking from the direction parallel to the drawing sheet of FIG. 1. As illustrated in FIG. 5, the irradiation unit 105 and the analysis unit 101 are connected to each other by an optical fiber 110. Similarly, the analysis unit 101 and the light receiving unit 106 are connected to each other by an optical fiber 110.

The above-mentioned components (i.e., the analysis unit 101, the irradiation unit 105, the light receiving unit 106, and the optical fibers 110) are accommodated in a case 111. While the case 111 has a size of about 200 mm×240 mm, for example, the size of the case 111 is not limited to those values.

As another example, a set of components included in the case 111 may be provided on one chip as a biochemical analysis device utilizing the MEMS (Micro-Electromechanical Systems) technology, e.g., μ-TAS (Micro-Total Analysis Systems). In such a case, the size of the case 111 can be further reduced.

<Wavelengths of Fluorescence from Serums in Diabetic Patient and Healthy Person>

FIG. 6 is a graph depicting measurement results of fluorescence attributable to AGEs (fluorescent substances) in serums of a diabetic patient and a healthy person. As seen from FIG. 6, the fluorescence intensity for the serum of the diabetic patient is significantly increased in comparison with that for the healthy person in a wavelength range of 420 nm or more.

Moreover, the inventors have discovered that the serum obtained from blood of the diabetic patient contain a significant amount of fluorescent substance, which generates fluorescence having a peak at a wavelength of about 440 nm when the serum is irradiated with excitation light having a peak at a wavelength of about 340 nm. That fluorescent substance is thought as being one type of AGEs.

One typical example of AGEs is pentosidine. Pentosidine emits fluorescence having a peak at a wavelength of about 385 nm upon irradiation with excitation light having a peak at a wavelength of about 335 nm. It can be hence said that a probability of the above-mentioned fluorescent substance being pentosidine is low.

With the analysis conducted by the inventors, AGEs contained in the serum of the diabetic patient are substances expressed by the following molecular formulae with a high possibility.

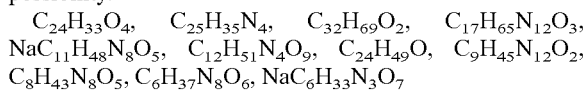

$C_{24}H_{33}O_4$, $C_{25}H_{35}N_4$, $C_{32}H_{69}O_2$, $C_{17}H_{65}N_{12}O_3$, $NaC_{11}H_{48}N_8O_5$, $C_{12}H_{51}N_4O_9$, $C_{24}H_{49}O$, $C_9H_{45}N_{12}O_2$, $C_8H_{43}N_8O_5$, $C_6H_{37}N_8O_6$, $NaC_6H_{33}N_3O_7$

Those substances have molecular weights in the range of 280 to 360 or the range of 385 to 490. Accordingly, by properly selecting the wavelength of the excitation light such that the fluorescent substances having molecular weights in the above-mentioned range are properly excited, the fluorescent substances possibly present in the blood or the serum after the artificial dialysis can be captured with higher reliability.

Furthermore, when the fluorescence having a peak at a wavelength of about 440 nm is measured from the serum obtained from the diabetic patient, this implies that the artificial dialysis has been ended in spite of AGEs being not sufficiently removed. In addition, there is a possibility that various diseases will be caused due to AGEs remained without being sufficiently removed.

In the artificial dialysis, therefore, it is preferable to end the artificial dialysis after specifying an amount of AGEs, which are contained in the blood, by some method, and confirming that the amount of AGEs contained in the blood has been sufficiently reduced.

In view of the above discussion, according to the present invention, the dialysis system 1 includes the dialysis end condition determining device 20 and the dialysis progress presenting device 21, as illustrated in FIG. 2. More appropriate management of the artificial dialysis is realized by utilizing the measurement result of the measuring device 10 in those two devices 20 and 21. Such a point will be described in detail below with reference to FIG. 7 illustrating the relationship among the measuring device 10, the dialysis end condition determining device 20, and the dialysis progress presenting device 21.

Figure 7:
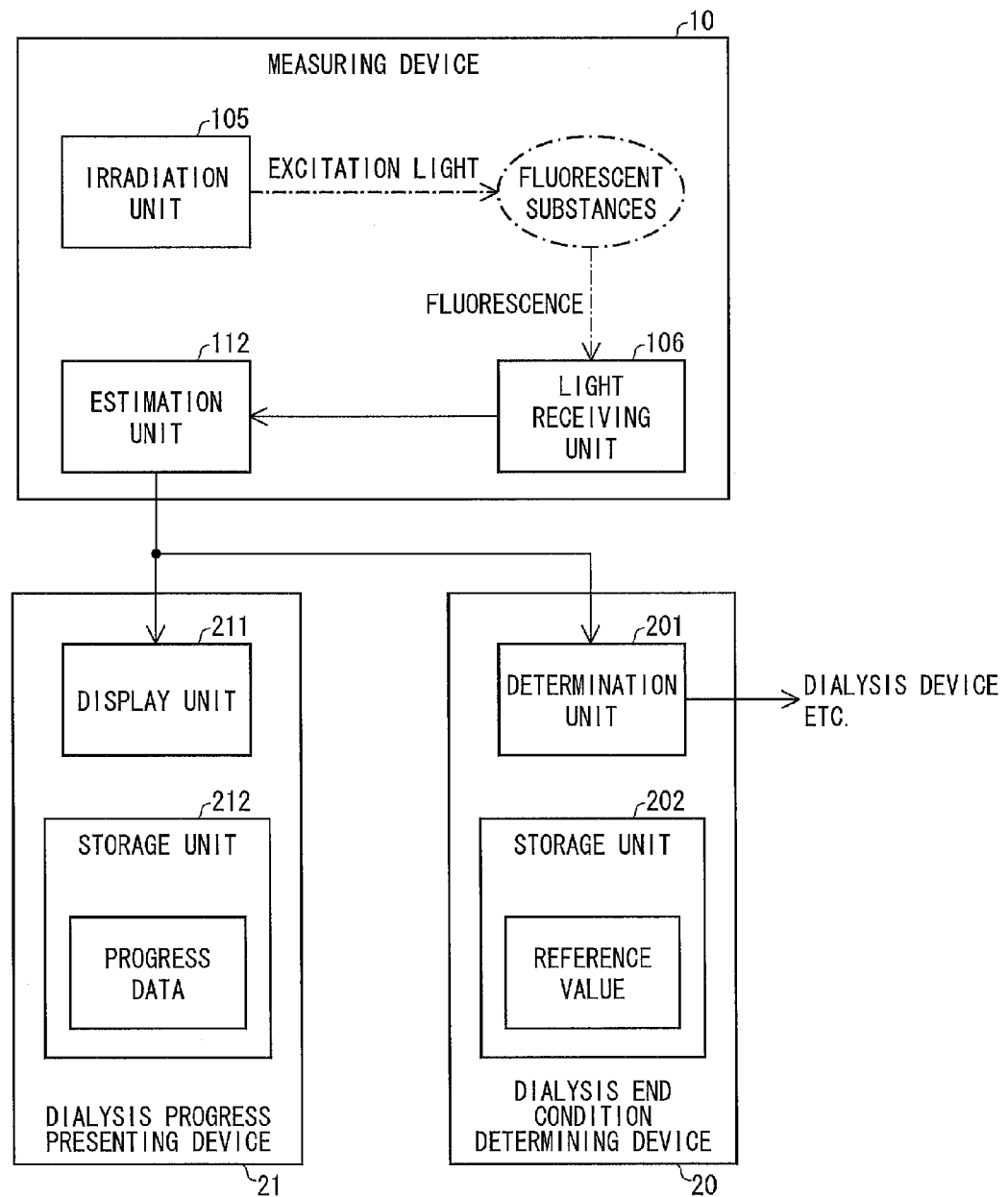
FIG. 7 is a block diagram illustrating configurations of the measuring device, a dialysis end condition determining device, and a dialysis progress presenting device in the dialysis system of FIG. 2.

As illustrated in FIG. 7, in the measuring device 10, the fluorescent substances are irradiated with the excitation light emitted from the irradiation unit 105, and fluorescence generated from the fluorescent substances is received by the light receiving unit 106. An estimation unit 112 accepts the measurement result of the intensity of the fluorescence received by the light receiving unit 106, and estimates the amount of the fluorescent substances based on the intensity of the fluorescence.

The arrangement of the estimation unit 112 is not limited to the case where the estimation unit 112 is included only in the measuring device 10, as illustrated in FIG. 7. In other words, each of the dialysis end condition determining device 20 and the dialysis progress presenting device 21 may include a unit similar to the estimation unit 112. Such an arrangement enables each of the dialysis end condition determining device 20 and the dialysis progress presenting device 21 to estimate the amount of the fluorescent substances based on the intensity of the fluorescence received by the light receiving unit 106 in the measuring device 10.

<Dialysis End Condition Determining Device 20>

The dialysis end condition determining device 20 includes a determination unit 201 and a storage unit 202. The determination unit 201 compares the amount of the fluorescent substances, which has been received from the estimation unit 112, with a reference value representing the amount of the fluorescent substances and used to determine the end of the dialysis. The storage unit 202 holds the reference value.

With the above-described configuration of the dialysis end condition determining device 20, when the amount of the fluorescent substances received from the estimation unit 112 is smaller than the reference value, i.e., when the fluorescent substances have been sufficiently removed from the blood under the artificial dialysis, the determination unit 201 can make determination that the dialysis may be finished. Thus, the determination unit 201 can finish the dialysis by transmitting such a determination result to the dialysis device 15, the blood pump 12, and so on.

By determining the end of the dialysis as described above, the artificial dialysis can be finished after reliable determination that the amount of the fluorescent substances contained in the blood has been sufficiently reduced.

<Dialysis Progress Presenting Device 21>

The dialysis progress presenting device 21 includes a display unit 211 and a storage unit 212. The display unit 211 continuously displays data (progress data), which represents the amount of the fluorescent substances, transmitted from the estimation unit 112 during the artificial dialysis. The storage unit 212 holds the progress data representing the amount of the fluorescent substances in the blood under the artificial dialysis after the start of the dialysis. By continuously presenting the amount of the fluorescent substances in the display unit 211 during the dialysis, it is possible to monitor an extent of removal of the fluorescent substances during the artificial dialysis in real time.

The number of measuring device 10 is not limited to only one with respect to the dialysis system 1 as in the case illustrated in FIG. 2. Two or more measuring devices may be disposed in one dialysis system. The dialysis end condition determining device and the dialysis progress presenting device may be disposed for each of the plural measuring devices. By disposing plural measuring devices, plural dialysis end condition determining devices, and plural dialysis progress presenting devices in one dialysis system as mentioned above, the amount of AGEs can be monitored at plural points in the dialysis system 1, and the artificial dialysis can be managed more appropriately.

<Recapitulation>

As described above, in the dialysis system 1, the measuring device 10 can measure the fluorescence generated from the fluorescent substances in the blood. The dialysis end condition determining device 20 can estimate the amount of the fluorescent substances from the measurement result of the fluorescence intensity, and can determine the dialysis end condition. The dialysis progress presenting device 21 can continuously present the amount of the fluorescent substances.

Here, AGEs in the blood can be handled as fluorescent substances. By incorporating, into the dialysis system 1, the dialysis progress presenting device 21 capable of monitoring the amount of AGEs during the artificial dialysis, therefore, values (such as a dialysis time, a concentration of the dialysis liquid, and a flow rate of the dialysis liquid) to be managed during the artificial dialysis, which have been determined so far from the empirical rules based on the past disease examples, etc., can be controlled in accordance with the amount of AGEs given as objective data. Furthermore, by determining the end of the artificial dialysis with the aid of the dialysis end condition determining device 20 such that AGEs will not remain in the blood, the artificial dialysis can be managed more appropriately.

[Recapitulation]

A measuring device according to a first aspect of the present invention comprises an analysis unit that holds blood or serum therein, an irradiation unit that irradiates fluorescent substances in the blood or the serum with excitation light, and a light receiving unit that receives fluorescence generated upon irradiation with the excitation light.

With the features described above, by irradiating the fluorescent substances in the blood or the serum held in the analysis unit with the excitation light from the irradiation unit, the fluorescent substances in the blood or the serum are excited and fluorescence is generated. By receiving the generated fluorescence by the light receiving unit, the fluorescence having the intensity correlated to an amount of the fluorescent substances in the blood or the serum can be measured. Accordingly, an amount of AGEs present as the fluorescent substances in the blood or the serum can be estimated from the measurement result of the fluorescence intensity. As a result, it is possible to monitor AGEs contained in the serum after the artificial dialysis or in the blood circulated during the artificial dialysis.

According to a second aspect of the present invention, in the measuring device according to the first aspect, the analysis unit preferably includes an inflow port through which the blood or the serum flows in, and has a capacity adapted to form a fluid pool of the blood or the serum when the blood or the serum is held in the analysis unit.

In the case of irradiating the blood or the serum with the excitation light and accurately measuring the fluorescence generated upon excitation of the fluorescent substances in the blood or the serum, it is desirable that a flow rate of the blood or the serum is close to 0.

With the features described above, the blood or the serum flowing into the analysis unit can be caused to temporarily reside as a pool in the analysis unit. The flow rate of the blood or the serum residing as the pool is close to 0. In other words, the fluorescence generated upon excitation of the fluorescent substances in the blood or the serum can be measured in a state where the flow rate of the blood or the serum is close to 0. As a result, an amount of the fluorescent substances in the blood or the serum can be accurately estimated from the measurement result of the fluorescence intensity.

According to a third aspect of the present invention, in the measuring device according to the second aspect, the analysis unit preferably includes a hole through which a syringe is inserted to sample the blood or the serum from the fluid pool.

With the feature described above, the blood or the serum can be sampled from the fluid pool by employing the syringe. Furthermore, serum can also be obtained, for example, by subjecting the sampled blood to, e.g., centrifugal separation. Moreover, respective amounts and structures of the fluorescent substances in the blood or the serum can be specified by analyzing the sampled serum or the serum, which is obtained through, e.g., the centrifugal separation, with liquid chromatography, for example.

According to a fourth aspect of the present invention, the measuring device according to any one of the first to third aspects preferably further comprises a mechanism that obtains the serum through centrifugal separation of the blood.

With the feature described above, the serum can be obtained by centrifuging the blood. Therefore, respective amounts and structures of the fluorescent substances in the serum can be specified by analyzing the obtained serum with liquid chromatography, for example.

According to a fifth aspect of the present invention, in the measuring device according to any one of the first to fourth aspects, when the blood or the serum branched from a flow passage, through which the blood or the serum flows at a first flow rate, flows into the analysis unit, the measuring device preferably further comprises a regulator that decelerates the blood or the serum flowing into the analysis unit to a second flow rate.

In the case of irradiating the blood or the serum with the excitation light and accurately measuring the fluorescence generated upon excitation of the fluorescent substances in the blood or the serum, the flow rate of the blood or the serum is required to be low.

With the feature described above, the blood or the serum having been decelerated by the regulator is held in the analysis unit. In other words, the fluorescence generated upon excitation of the fluorescent substances in the blood or the serum can be measured in a state where the flow rate of the blood or the serum is low. As a result, an amount of the fluorescent substances in the blood or the serum can be accurately estimated from the measurement result of the fluorescence intensity.

According to a sixth aspect of the present invention, in the measuring device according to the fifth aspect, the second flow rate is preferably 10 ml/min or less.

In the case of irradiating the blood or the serum with the excitation light and more accurately measuring the fluorescence generated upon excitation of the fluorescent substances in the blood or the serum, the flow rate of the blood or the serum is preferably 10 ml/min or less.

With the feature described above, the blood or the serum having been decelerated to 10 ml/min or less is held in the analysis unit. In other words, the fluorescence generated upon excitation of the fluorescent substances in the blood or the serum can be measured in a state where the flow rate of the blood or the serum is 10 ml/min or less. As a result, an amount of the fluorescent substances in the blood or the serum can be more accurately estimated from the measurement result of the fluorescence intensity.

According to a seventh aspect of the present invention, in the measuring device according to the first aspect, the analysis unit is preferably a drip chamber.

With the feature described above, since the analysis unit is a drip chamber, the flow rate of the blood or the serum can be held closer to 0 in the drip chamber even when the measuring device has a simple configuration in which the blood or the serum is not branched and the regulator is not included. In other words, the fluorescence generated upon excitation of the fluorescent substances in the blood or the serum of which flow rate is closer to 0 can be measured with the simple configuration. As a result, an amount of the fluorescent substances in the blood or the serum can be accurately estimated from the measurement result of the fluorescence intensity with the simple configuration.

According to an eighth aspect of the present invention, in the measuring device according to any one of the first to seventh aspects, the analysis unit is preferably made of quartz.

In the case of irradiating the blood or the serum with the excitation light and satisfactorily measuring the fluorescence generated upon excitation of the fluorescent substances in the blood or the serum, the light receiving unit is required to receive the fluorescence generated with higher intensity from the same amount of fluorescent substances. It is known that quartz is highly permeable to light of a wider range of wavelength including ultraviolet rays.

With the feature described above, since the excitation light passes through the analysis unit with higher transmittance, the fluorescent substances in the analysis unit are more strongly excited, and stronger fluorescence is generated from the same amount of fluorescent substances. The stronger fluorescence thus generated is received by the light receiving unit after passing through the analysis unit with higher transmittance. As a result, an amount of the fluorescent substances in the blood or the serum can be satisfactorily estimated from the measurement result of the fluorescence intensity.

According to a ninth aspect of the present invention, in the measuring device according to any one of the first to eighth aspects, preferably, a peak wavelength of the excitation light is in a range of 338 to 342 nm, and a peak wavelength of the fluorescence is in a range of 420 to 460 nm.

A particular fluorescent substance generates fluorescence of a particular wavelength upon irradiation with excitation light of a particular wavelength.

With the features described above, by irradiating the blood or the serum with excitation light of a first particular wavelength and by measuring fluorescence of a second particular wavelength generated upon excitation of the fluorescent substances in the blood or the serum, an amount of particular one or more of the fluorescent substances in the blood or the serum can be estimated from the measurement result of the fluorescence intensity.

In the above-described measurement, when there is only one fluorescent substance corresponding to a pair of the excitation light of the particular wavelength and the fluorescence of the particular wavelength, an amount of the particular one fluorescent substance in the blood or the serum can be accurately estimated from the measurement result of the fluorescence intensity.

According to a tenth aspect of the present invention, in the measuring device according to any one of the first to ninth aspects, the fluorescent substances preferably have molecular weights in a range of 280 to 360 or a range of 385 to 490.

With the feature described above, the fluorescent substances, which are thought as being still present in the blood or the serum after artificial dialysis, can be captured with higher reliability.

A dialysis end condition determining device according to an eleventh aspect of the present invention includes a determination unit that compares an amount of fluorescent substances, which is estimated from a measurement result of fluorescence intensity obtained by measuring the intensity of fluorescence by the measuring device according to any one of the first to tenth aspects, with a predetermined reference value, and that determines, based on a comparison result, whether a dialysis end condition is satisfied.

With the feature described above, the amount of the fluorescent substances estimated from the measurement result of the fluorescence intensity, which has been measured by the measuring device, is compared with a predetermined reference value, and whether the dialysis end condition is satisfied can be determined based on the comparison result. In other words, the dialysis can be finished by comparing the amount of the fluorescent substances with the predetermined reference value. This implies that the dialysis can be finished by determining the state where the amount of the fluorescent substances in an object of the dialysis is reduced to the predetermined reference value or less. Therefore, the fact that the fluorescent substances such as AGEs, which are regarded to be harmful to human bodies, have been removed from the object of the dialysis, can be quantitatively ensured in accordance with objective data, i.e., the remaining amount of the fluorescent substances. Thus, quality of the artificial dialysis can be maintained by finishing the artificial dialysis based on the amount of the fluorescent substances.

A dialysis progress presenting device according to a twelfth aspect of the present invention includes a presentation unit that continuously presents an amount of fluorescent substances, which is estimated from a measurement result of fluorescence intensity obtained by measuring the intensity of fluorescence by the measuring device according to any one of the first to tenth aspects.

With the feature described above, the amount of the fluorescent substances can be continuously presented which is estimated from the fluorescence intensity measured by the measuring device. In other words, the progress of change in the amount of the fluorescent substances can be presented during the dialysis. Therefore, the progress indicating how far the amount of the fluorescent substances in the object of the dialysis has been reduced can be presented during the dialysis. It is hence possible to, during the artificial dialysis, present in real time the amount of the fluorescent substances based on the result of measuring the intensity of the fluorescence that is generated from the fluorescent substances in the blood or the serum, and to realize more appropriate management of the artificial dialysis.

It is to be noted that the present invention is not limited to the above-described embodiment, and it can be variously modified within the scope defined in Claims. In other words, embodiments resulting from combining technical means with each other, which are modified as appropriate within the scope defined in Claims, are also involved within the technical scope of the present invention.

INDUSTRIAL APPLICABILITY

The present invention can be suitably applied to, in addition to the determination about the end condition in ordinary artificial dialysis, evaluation of, e.g., the performance of a dialyzer to remove the fluorescent substances by executing fluorescence measurement in stage before and after the dialyzer. The present invention can be further suitably applied to determination about the end condition and evaluation of the performance in removing the fluorescent substances in peritoneum dialysis (PD), for example, by not only measuring the fluorescent substances in the blood or the serum, but also by executing the fluorescence measurement on the dialysis liquid after the fluorescent substances have been removed from the object of the artificial dialysis. Moreover, the present invention can be suitably applied to, e.g., inspection and preventive instruments for adult diseases, such as diabetes and diabetic complications, and health management systems, as well as to the artificial dialysis.

REFERENCE SIGNS LIST 1 dialysis system
2 arm
10 measuring device
11 artery shunt
12, 109 blood pump
13 artery-side drip chamber
14 dialyzer
15 dialysis device
16 vein-side drip chamber
17 branch valve
18 vein shunt
20 dialysis end condition determining device
21 dialysis progress presenting device
101, 101a, 101b analysis unit
102 inflow port
103 outflow port
104 regulator
105 irradiation unit
106 light receiving unit
107 syringe sampling portion (hole)
108 syringe
110 optical fiber
111 case
112 estimation unit
201 determination unit
202, 212 storage unit
211 display unit
B fluid pool

The invention claimed is:

1. A measuring device comprising:
an analysis unit that holds blood or serum therein;
an irradiation unit that irradiates fluorescent substances in the blood or the serum with excitation light; and
a light receiving unit that receives fluorescence generated upon irradiation with the excitation light, wherein
the analysis unit includes:
an inflow port through which the blood or the serum flows in; and
an outflow port through which the blood or the serum flows out; wherein
when inflow and outflow of the blood or the serum are in an equilibrium state, a fluid pool of the blood or the serum is formed inside the analysis unit;
the analysis unit is a drip chamber;
the fluid pool of the blood or serum is located inside of the drip chamber;
the irradiation unit is positioned outside the drip chamber and irradiates fluorescent substances in the fluid pool with excitation light through a wall of the drip chamber;
the light receiving unit is positioned outside the drip chamber and receives fluorescence in the fluid pool with the excitation light through a portion of the wall of the drip chamber, the portion contacting the fluid pool; and
the blood or the serum is irradiated with the excitation light from the irradiation unit in a direction that is perpendicular to a direction in which the fluorescence is received by the light receiving unit.

2. The measuring device according to claim 1, wherein the analysis unit includes a hole through which a syringe is inserted to sample the blood or the serum from the fluid pool.

3. The measuring device according to claim 1, wherein the measuring device obtains the serum through centrifugal separation of the blood.

4. The measuring device according to claim 1, wherein when the blood or the serum branched from a flow passage, through which the blood or the serum flows at a first flow rate, flows into the analysis unit, the measuring device further comprises a regulator that decelerates the blood or the serum flowing into the analysis unit to a second flow rate.

5. The measuring device according to claim 4, wherein
the regulator is a needle valve; and
the second flow rate is regulated to be 10 ml/min or less by rotating a needle of the needle valve.

6. The measuring device according to claim 1, wherein the analysis unit is made of quartz.

7. The measuring device according to claim 1, wherein the irradiation unit irradiates the fluorescent substances in the blood or the serum with the excitation light having a peak wavelength in a range of 338 to 342 nm; and the light receiving unit receives the fluorescence having a peak wavelength in a range of 420 to 460 nm.

8. A dialysis end condition determining device including:
the measuring device according to claim 1; and
a determination unit that is connected to the measuring device and compares an amount of fluorescent substances, which is estimated from a measurement result of fluorescence intensity obtained by measuring the intensity of fluorescence by the measuring device, with a predetermined reference value, and that determines, based on a comparison result, whether a dialysis end condition is satisfied.

9. A dialysis progress presenting device including:
the measuring device according to claim 1; and
a presentation unit that is connected to the measuring device and continuously presents an amount of fluorescent substances, which is estimated from a measurement result of fluorescence intensity obtained by measuring the intensity of fluorescence by the measuring device.

* * * * *